United States Patent [19]

Hughes

[11] Patent Number: 4,654,433

[45] Date of Patent: Mar. 31, 1987

[54] PROCESS FOR THE PREPARATION OF ESTERS OF AMINO ACIDS

[75] Inventor: David L. Hughes, Scotch Plains, N.J.

[73] Assignee: Merck & Co., Inc., Rahway, N.J.

[21] Appl. No.: 691,086

[22] Filed: Jan. 14, 1985

[51] Int. Cl.$^4$ .................................... C07C 101/77
[52] U.S. Cl. ........................................ 560/40; 560/38; 560/153; 560/155; 560/169; 560/170; 560/173; 546/242; 546/316; 548/312; 548/547
[58] Field of Search ................. 560/38, 153, 155, 169, 560/170, 173; 546/316, 242; 548/312, 547

[56] References Cited

PUBLICATIONS

Saari et al., *J. Med. Chem.*, vol. 21, No. 8, pp. 746–753, (1978).

Frost et al., *Kinetics and Mechanisms*, Wiley, New York, pp. 138–144, (1953).

Pocker et al., *J. Am. Chem. Soc.*, vol. 99, No. 7, pp. 2276–2284 (1977).

Fieser et al., *Reagents for Organic Synthesis*, p. 1303, (1967).

Primary Examiner—Natalie Trousof
Assistant Examiner—Bruce D. Gray
Attorney, Agent, or Firm—Alice O. Robertson; Michael C. Sudol

[57] ABSTRACT

A simple single step process for preparing alkyl and substituted alkyl esters of amino acids is described. The products are bioactive compounds including compounds useful as antihypertensive agents.

15 Claims, No Drawings

PROCESS FOR THE PREPARATION OF ESTERS OF AMINO ACIDS

The present invention is directed to a process for the preparation of alkyl and substituted alkyl esters of amino acids, more particularly, to an improved single step process for the their preparation.

BACKGROUND OF THE INVENTION

Amino acids embrace many naturally occurring materials and as well many unnatural compounds which have high therapeutic utility. One amino acid which is especially useful as an antihypertensive agent is α-methyldopa, chemically identified as (S)-3-(3,4-dihydroxyphenyl)-2-methylalanine. While the compound has been administered orally as the acid salt, for certain applications the ester form is desirable. Ethyl ester of methyldopa hydrochloride is currently employed for intravenous application. In U.S. Pat. No. 3,983,138 there are disclosed esters and derivatives of α-methyldopa which are active in the treatment of hypertension, and it is further disclosed that some of these compounds have much higher activity than α-methyldopa itself. One of the esters described in the patent is especially useful, namely, the α-pivaloyloxyethyl ester and the preparation of said ester in good yields is especially desirable. U.S. Pat. No. 4,440,942 describes the preparation of a crystalline form of diastereomeric L-α-methyldopa POE ester by a reaction carried out in an atmosphere of nitrogen with the application of heat for an extended period. While this method is an improvement over earlier methods, a method which produces better yields and consistent good yields is still desired.

DESCRIPTION OF THE INVENTION

According to the present invention it has been discovered that alkyl or substituted alkyl esters of amino acids may be prepared in consistently high yields by a simple single step process which comprises intimately contacting an amino acid and an alkylating agent in a selected aprotic solvent in the presence of excess ionizing salt for time sufficient to complete the reaction. Preferably, the reaction is also carried out in the presence of molecular sieves.

One of the key advantages of the present process is that the operation may be carried out at temperatures generally lower than that heretofore employed and for a shorter time thereby producing products of higher purity and greater stability. Moreover the lower temperature and shorter time constitute a further advantage in terms of savings in time and energy. In addition, the process does not require the provision of a nitrogen atmosphere as does the known process.

"Amino acids38 embraced by the process of the present invention includes substantially all amino acids in which the amino group is a primary amino group which must normally be protected when the carboxyl group is subjected to alkylation for the purpose of preparing an ester compound. Thus, amino acids include valine, leucine, norleucine, phenylalanine; hydroxy substituted amino acids such as serine, threonine and tyrosine; and sulfur amino acids such as methionine. Basic amino acids such as lysine and ornithine may be employed also if employed as their acid salts. Also embraced in the scope of the amino acids are 3-(3,4-dihydroxyphenyl)-2-methylalanine, 3-(3,4-dihydroxyphenyl)alanine, and the like. The levo isomer of 3-(3,4-dihydroxyphenyl)-2-methylalanine, and of sinister configuration, is the drug known as methyldopa or α-methyldopa. α-Methyldopa as hereinafter employed is to be understood to refer to (S)-3-(3,4-dihydroxyphenyl)-2-methylalanine.

The alkylating agents which may be employed in the process of the present invention may be any alkylating agent which on reaction with the carboxyl group of the amino acid would form the desired alkyl or substituted alkyl ester. The ester forming group in the alkylating agent embraces substituted alkyl groups, such as aralkyl, alkoxyalkyl, alkylthioalkyl, acyloxyalkyl, acylaminoalkyl, acyliminoalkyl, mono and polyhaloalkyl and the like. The alkylating agents may be represented by

$$J-C_nH_{2n}-Y$$

wherein n is at least 1 and J may be hydrogen, alkyl, alkoxy, alkylthio, halo, haloalkyl, polyhaloalkyl, aryl, acyloxy, acylamino, acylimino wherein acyl may be open chain or may be joined through the imino nitrogen in a heterocyclic structure, or J may form part of a heterocyclic nucleus such as a hydantoin nucleus. Further, acyl as herein employed is intended to represent a group originating from an acid function and therefore embraces those derived from heterocyclic acids such as, for example, nicotinic acid. The leaving group, y, may be halide, methylsulfate, tosylate and the like. Generally, halides are preferred. Various types of alkylating agents may be represented by specific alkylating agents such as methyl bromide, ethyl bromide, isopropyl bromide, benzyl bromide, β-phenylethyl bromide, α-chloroethyl pivalate, N-bromomethylsuccinimide, N-(1-chloroethyl)succinimide, N-(2-chloroethyl)-2,2,2-trifluoroacetamide, 2-(chloroethyl)nictoinamide, chloromethyl pivalate, 1-chloro-1-succinimideopropane, N-chloromethylglutarimide, 1-methyl-3-chloromethylhydantoin, 2-phenoxyethyl bromide, 2-chloroethyl acetate, N-(2-chloroethyl)-benzamide, N-chloromethylnaphthalimide, and the like.

By "ionizing salts" is meant inorganic or quaternary ammonium salts which increase the polarity of the reaction medium. Suitable salts include alkali metal halides, i.e., chloride, bromide, iodide, alkali metal chlorates, alkali metal acetates, alkaline earth metal halides, and the like. The preferred salts are alkali metal halides. Specific salts which may be employed include lithium bromide, lithium iodide, lithium chloride, sodium bromide, sodium iodide, sodium nitrate, lithium perchlorate, potassium iodide, tetra(n-butyl)ammonium iodide, tetraethylammonium iodide, benzyltrimethylammonium iodide and the like. Mixtures of salts also may be employed.

The reaction medium is an aprotic solvent. It has been found that the selection of the appropriate solvent is critical to the obtaining of good yields. The most useful solvents for consistent good yields were found to be N-methylpyrrolidinone and tetramethylurea. Thus, these are the preferred solvents for the process and for certain esters, the only useful solvents for the good yields contemplated. For others, other solvents such as 1,3-dimethylimidazolidinone, and the like may be employed.

The expression "sieves" as herein employed, sometimes called "molecular sieves," are alumino-silicate powders useful for adsorbing water or small molecules. The sieves have standard type designation corresponding to pore diameter (in angstroms) and are available commercially as powders, pellets or beads. 4A sieves, preferably in powdered form, have been found to be useful in the present process. Although good yields have been obtained without the use of sieves, it has been found that even better yields of the order of 6 to 12 percent or higher may be achieved by the use of sieves.

In the reaction, approximately equimolar amounts of the amino acid and alkylating agent are employed. It is preferable to have a slight excess of the alkylating agent. Generally about 10 to 20 mole percent excess is employed, i.e., the mole ratio of amino acid to alkylating agents is from about 1:1.1 to about 1:1.2.

The ionizing salt is preferably employed in molar excess, generally, from about 1.5 to 4 molar excess. An about two molar excess amount gives good results.

The amount of the sieves will vary from 0 to about ½ of the weight of the amino acid employed.

The amount of the aprotic solvent may be from about 4.5 to 15 times the weight of the amino acid employed. Increasing or decreasing the concentration of amino acid tends to lower the yields.

The temperature suitable for the reaction is in the range of from about 10° C. to about 80° C. The preferred range is from about 20° to about 60° C.

The reaction may be carried out simply by mixing the reactants, the ionizing salt and sieve, if employed, in an aprotic solvent at ambient temperature or with slight heating for time sufficient to complete the reaction with the formation of the desired ester product. Usually the reaction is complete in a few hours. Alternatively, the alkylating agent may be added in a portionwise manner. This may be carried out by a continuous metered addition, or by addition of portions at spaced intervals. After completion of the reaction by either method, the reaction mixture may be subjected to conventional separation and purification procedures.

The following examples illustrate the invention but are not to be construed as limiting.

EXAMPLE I

α-Pivaloyloxyethyl (S)-3-(3,4-dihydroxyphenyl)-2-methylalaninate 10 grams (0.047 mole) of α-methyldopa, 4.7 grams of powdered 4A molecular sieves, 6.1 grams (0.070 mole) of lithium bromide and 47 milliliters of N-methylpyrrolidinone were stirred for about one hour at 25° C. To this mixture, 8.1 grams (0.049 mole) of α-chloroethyl pivalate was added and the mixture was aged at 55° C. for 8 hours. At the end of this time, the mixture was cooled to 25° C., diluted with 100 milliliters of ethyl acetate and washed successively with one 200 milliliter and two 100 milliliter portions of saturated sodium bicarbonate solution. The combined sodium bicarbonate washes were extracted with two 100 milliliter portions of ethyl acetate and the combined ethyl acetate extracts concentrated under vacuum to 150 milliliters. The assay yield of α-pivaloyloxyethyl (S)-3-(3,4-dihydroxyphenyl)-2-methylalaninate was found to be 14.4 grams or 90 percent of theoretical.

EXAMPLE II

In a similar operation, 1.05 grams of α-methyldopa, 0.87 gram of lithium bromide, 0.43 gram of sieves, 0.98 gram of 90 percent chloroethyl pivalate and 5.00 grams of N-methylpyrrolidinone were mixed together and gradually warmed to about 80° C. over a period of about an hour and maintained at this temperature for over two hours. Assays of samples taken after about one hour and about two hours by high pressure liquid chromatography showed yields of the desired product to be over 80 percent both times.

EXAMPLE III

A similar operation was carried out except that α-chloroethyl pivalate was added in a stepwise manner, approximately one-quarter of the total amount at a time.

Initially, 1.05 grams (5.0 millimoles) of α-methyldopa, 0.50 gram of sieves, 0.80 gram (9.2 millimoles) of lithium bromide, 5.03 grams of N-methylpyrrolidinone and 0.25 gram of α-chloroethyl pivalate were stirred together. Thereafter at hourly intervals, 0.29 gram, 0.31 gram and 0.27 gram of α-chloroethyl pivalate were added and the stirring continued. A total of 0.87 gram (6.1 millimoles) was added. The temperature of the reaction mixture was in the range of 45° to 53° C. Stirring was continued and about three hours after the completion of the addition. A high pressure liquid chromatographic assay made on a 25 milliliter sample indicated 83 percent (area percent) of α-pivaloyloxyethyl (S)-3-(3,4-dihydroxyphenyl)-2-methylalaninate product. An assay after 24 hours of stirring at ambient temperature indicated the yield of the α-pivaloyloxyethyl ester product to be about 86 percent.

EXAMPLE IV

Benzyl (S)-3-(3,4-Dihydroxyphenyl)-2-methylalaninate

In a manner similar to that described in Example I, 1.05 grams (0.005 mole) of α-methyldopa, 0.88 gram (0.010 mole) of lithium bromide, 0.5 gram of powdered 4A sieves, 0.98 gram (0.0057 mole) of benzyl bromide and 5.0 grams of N-methylpyrrolidinone were stirred for 65 hours at 25° C. At the end of this period, high pressure liquid chromatographic assay showed an 85 percent yield of the desired benzyl (S)-3-(3,4-dihydroxyphenyl)-2-methylalaninate product.

EXAMPLE V

Methyl (S)-3-(3,4-Dihydroxyphenyl)-2-methylalaninate

In a manner similar to the preceding examples, 1.05 grams (0.005 mole) of o-methyldopa, 0.88 gram (0.010 mole) of lithium bromide, 0.5 gram of powdered 4A sieves, 0.85 gram (0.006 mole) of methyl iodide and 5.0 gram of N-methylpyrrolidinone were stirred together for 5 hours at 50° C. to obtain the desired methyl (S)-3-(3,4-dihydroxyphenyl)-2methylalaninate product. A high pressure liquid chromatographic assay showed the yield to be 75 percent.

EXAMPLE VI

Benzyl Phenylalaninate 1.64 grams (0.010 mole) of phenylalanine, 1.76 grams (0.020 mole) of lithium bromide, 2.03 grams (0.012 mole) of benzyl bromide and 11 grams of N-methylpyrrolidinone were stirred together for 16 hours at 25° C. and for 2 hours at 50° C. A high pressure liquid chromatographic assay made at this time showed 82 percent conversion to the benzyl phenylalaninate product.

The product was isolated as the p-tosylate salt by first adding 70 milliliters of ethyl acetate to the reaction mixture, then washing the resulting mixture with three 50 milliliter portions of saturated sodium bicarbonate solution. The washed solution was then diluted to 200 milliliters with additional ethyl acetate, 1.7 grams (0.009 mole) of p-toluenesulfonic acid monohydrate added thereto and the resulting mixture maintained for 3 hours

EXAMPLE VII

Benzyl α-amino-β-hydroxypropionate

In a similar manner 1.09 grams (0.0105 mole) of serine, 1.76 grams (0.02 mole) of lithium bromide, 2.02 grams (0.0118 mole) of benzyl bromide and 16 grams of N-methylpyrrolidinone were stirred together at 25° C. for 16 hours and at 50° C. for 3 hours to obtain the desired benzyl α-amino-β-hydroxypropionate product. High pressure liquid chromatographic assay indicated a 86 percent yield of the desired product.

EXAMPLE VIII

Benzyl Alaninate

In a similar operation, 0.45 gram (0.005 mole) of alanine, 0.87 gram (0.01 mole) of lithium bromide, 0.95 gram (0.0055 mole) of benzyl bromide and 4.8 grams of N-methylpyrrolidinone were stirred together for 5.5 hours at 55° C. to obtain the desired benzyl alaninate product. High pressure liquid chromatographic assay showed yield of the product to be 89 percent.

EXAMPLE IX

In operations carried out in a similar manner the following esters may be prepared:

Succinimidomethyl (S)-3-(3,4-dihydroxyphenyl)-2-methylalaninate by the reaction of α-methyldopa and N-bromomethylsuccinimide in the presence of lithium bromide in N-methylpyrrolidinone.

α-Succinimidoethyl (S)-3-(3,4-dihydroxyphenyl)-2-methylalaninate by the reaction of α-methyldopa and N-(1-chloroethyl)succinimide in the presence of lithium bromide in N-methylpyrrolidinone.

2-Trifluoroacetamidoethyl (S)-3-(3,4-dihydroxyphenyl)-2-methylalaninate by the reaction of α-methyldopa and N-(2-chloroethyl)-2,2,2-trifluoroacetamide in the presence of lithium bromide in N-methylpyrrolidinone.

2-Nicotinamidoethyl (S)-3-(3,4-dihydroxyphenyl)-2-methylalaninate by the reaction of α-methyldopa and N-(2-chloroethyl)nicotinamide in the presence of lithium bromide in N-methylpyrrolidinone.

Glutarimidomethyl (S)-3-(3,4-dihydroxyphenyl)-2-methylalaninate by the reaction of α-methyldopa and N-chloromethylglutarimide in the presence of tetra(n-butyl)ammonium iodide in N-methylpyrrolidinone.

1-Methyl-3-[(S)-3-(3,4-dihydroxyphenyl)-2-methylalanyloxymethyl]hydantoin by the reaction of α-methyldopa and 1-methyl-3-chloromethylhydantoin in the presence of lithium bromide in tetramethylurea.

What is claimed is:

1. A process for preparing an alkyl or substituted alkyl ester of an amino acid wherein in said ester the amino acid is one in which the amino group is a primary amino group and wherein the ester group is lower alkyl, aralkyl, alkoxyalkyl, alkylthioalkyl, acyloxyalkyl, acylaminoalkyl, acyliminoalkyl, haloalkyl, polyhaloalkyl, and heterocycloalkyl, which comprises intimately contacting such amino acid with an alkylating agent in an aprotic solvent selected from N-methylpyrrolidinone and tetramethylurea in the presence of from about 1.5 to 4 molar excess ionizing salt and up to ½ the weight of the amino acid of molecular sieves for time sufficient to complete the reaction wherein said alkylating agent is represented by $$J-C_nH_{2n}-Y$$

wherein n is at least 1, J is selected from the group consisting of hydrogen, alkyl, alkoxy, alkylthio, halo, haloalkyl, polyhaloalkyl, aryl, acyloxy, acylamino, and acylimino wherein acyl is open chained or is joined through the imino nitrogen in a heterocyclic structure or J is a part of hydantoin or heterocyclic nucleus and Y is selected from the group consisting of halide, methyl sulfate, and tosylate; and wherein said ionizing salt is selected from the group consisting of alkali metal halide and quaternary ammonium halide.

2. A process according to claim 1 in which the amino acid is an α-amino acid.

3. A process according to claim 1 wherein the ionizing salt is an alkali metal halide.

4. A process according to claim 2 wherein the ionizing salt is employed in an amount of from about 1.5 to 2 molar proportions for each molar proportion of amino acid and alkylating agent.

5. A process according to claim 1 wherein the alkylating agent is a lower alkyl halide or a substituted lower alkyl halide.

6. A process according to claim 1 wherein the α-amino acid is 30(3,4-dihydroxyphenyl)-2-methylalanine.

7. A process according to claim 6 wherein the 3-(3,4-dihydroxyphenyl)-2-methylalanine is the (S)-isomer.

8. A process according to claim 6 wherein the alkylating agent is 1-chloroethyl pivalate.

9. A process according to claim 6 wherein the alkylating agent is benzyl bromide.

10. A process according to claim 6 wherein the alkylating agent is methyl iodide.

11. A process according to claim 6 wherein the alkylating agent is ethyl bromide.

12. A process for preparing an alkyl or substituted alkyl ester of an amino acid wherein in said ester the amino acid is one in which the amino group is a primary amino group and wherein the ester group is lower alkyl, aralkyl, alkoxyalkyl, alkylthioalkyl, acyloxyalky, acylaminoalkyl, acyliminoalkyl, haloalkyl, polyhaloalkyl, and heterocycloalkyl, which comprises intimately contacting such amino acid with an alkylating agent in an aprotic solvent selected from N-methylpyrrolidinone and tetramethylurea in the presence of from about 1.5 to 4 molar excess ionizing salt and up to ½ the weight of amino acid of molecular sieves for time sufficient to complete the reaction wherein said alkylating agent is represented by $$J-C_nH_{2n}-Y$$

wherein n is at least 1, J is selected from the group consisting of hydrogen, alkyl, alkoxy, alkylthio, halo, haloalkyl, polyhaloalkyl, aryl, acyloxy, acylamino, and acylimino wherein acyl is open chained or is joined through the imino nitrogen in a heterocyclid structure or J is a part of hydantoin or heterocyclic nucleus and Y is halide; and wherein said ionizing salt is selected from the group consisting of alkali metal halide and guaternary ammonium halide and wherein the amount of the aprotic solvent is from about 4.5 to 15 times the weight of the amino acid employed.

13. A process for preparing (S)-1-pivaloyloxyethyl (S)-3-(3,4-dihydroxphenyl)-2-methylalaninate which comprises intimately contacting (S)-3-(3,4-dihydroxyphenyl)-2-methylalanine and 1-chloroethyl pivalate in N-methylpyrrolidinone or tetramethylurea in the presence of from about 1.5 to 4 molar excess alkali metal or quaternary ammonium halide and up to ½ the weight of the amino acid of molecular sieves for time sufficient to complete the reaction.

14. A process for preparing (S)-1-pivaloyloxyethyl (S)-3-(3,4-dihydroxyphenyl)-2-methylalaninate which comprises intimately contacting (S)-3-(3,4-dihydroxyphenyl)-2-methylalanine and 1-chloroethyl pivalate in N-methylpyrrolidinone or tetramethylurea in the presence of from about 1.4 to 4 molar excess lithium bromide and molecular sieves for time sufficient to complete the reaction.

15. A process according to claim 14 wherein the lithium bromide is employed in an amount of 2 molar proportions for each molar proportion of the amino acid and alkylating agent.

* * * * *